(12) United States Patent
Yahalomi et al.

(10) Patent No.: US 6,861,553 B2
(45) Date of Patent: Mar. 1, 2005

(54) PROCESS FOR PREPARING NATEGLINIDE AND INTERMEDIATES THEREOF

(75) Inventors: Ronit Yahalomi, Kiryat Bialik (IL); Evgeny Shapiro, Haifa (IL); Ben-Zion Dolitzky, Petach Tiqva (IL); Yigael Gozlan, Ramot Sapir (IL)

(73) Assignee: Teva Pharmaceuticals Industries Ltd., Petah Tiqva (IL)

( * ) Notice: Subject to any disclaimer, the term of this patent is extended or adjusted under 35 U.S.C. 154(b) by 27 days.

(21) Appl. No.: 10/614,266

(22) Filed: Jul. 3, 2003

(65) Prior Publication Data

US 2004/0152782 A1 Aug. 5, 2004

Related U.S. Application Data

(60) Provisional application No. 60/449,791, filed on Feb. 24, 2003, provisional application No. 60/442,109, filed on Jan. 23, 2003, provisional application No. 60/432,962, filed on Dec. 12, 2002, provisional application No. 60/432,093, filed on Dec. 10, 2002, provisional application No. 60/423,750, filed on Nov. 5, 2002, provisional application No. 60/414,199, filed on Sep. 26, 2002, provisional application No. 60/413,622, filed on Sep. 25, 2002, provisional application No. 60/369,904, filed on Jul. 18, 2002, and provisional application No. 60/393,495, filed on Jul. 3, 2002.

(51) Int. Cl.$^7$ ............................................. C07C 239/00
(52) U.S. Cl. ....................................... 562/450; 514/563
(58) Field of Search .......................... 562/450; 514/563

(56) References Cited

U.S. PATENT DOCUMENTS

| 4,816,484 A | 3/1989 | Toyoshima et al. |
|---|---|---|
| RE34,878 E | 3/1995 | Toyoshima et al. |
| 5,463,116 A | 10/1995 | Sumikawa et al. |
| 5,488,150 A | 1/1996 | Sumikawa et al. |
| 6,548,529 B1 | 4/2003 | Robl et al. |
| 6,555,519 B2 | 4/2003 | Washburn |
| 2001/0044584 A1 | 11/2001 | Kensey |
| 2002/0032149 A1 | 3/2002 | Kensey |
| 2002/0061835 A1 | 5/2002 | Kensey |
| 2003/0069221 A1 | 4/2003 | Kosoglou et al. |
| 2003/0078517 A1 | 4/2003 | Kensey |

FOREIGN PATENT DOCUMENTS

| SK | 200200360 | 7/2002 |
|---|---|---|
| WO | WO 01/21159 | 3/2001 |
| WO | WO 02/32854 | 4/2002 |
| WO | WO 02/32854 A1 * | 4/2002 |
| WO | WO 02/34254 | 5/2002 |
| WO | WO 02/34285 | 5/2002 |
| WO | WO 02/34713 | 5/2002 |
| WO | WO 02/40010 | 5/2002 |
| WO | WO 03/022251 | 3/2003 |
| WO | WO 03/076393 | 9/2003 |
| WO | WO 03/087038 | 10/2003 |
| WO | WO 03/087039 | 10/2003 |
| WO | WO 03/093222 | 11/2003 |

OTHER PUBLICATIONS

CA 123:55430 for JP 07017899, Tohishiro et al, (1995).*
U.S. Appl. No. 10/622,905, Yahalomi et al., filed Jul. 18, 2003.
Hiroko Takesada et al., "Structure Determination of Metabolites Isolated from Urine and Bile after Administration of AY4166, a Novel α–Phenylalanine–Derivative Hypoglycemic Agent," Bioorganic & Medicinal Chemistry, vol. 4, No. 10, 1996, pp. 1771–1781.
Hisashi Shinkai et al., "N–(Cyclohexylcartonyl)–D–phenylalanines and Related Compounds. A New Class of Oral Hypoglycemic Agents. 2," J. Med. Chem., Vol 32, 1989, pp. 1436–1441.
Xue–yan Zhu et al., "Study on Synthesis of Nateglinide," Hecheng Huaxue, vol. 9, No. 6, 2001, pp. 537–540.
Li Gang et al., "A New Crystal Form of Nateglinide," Acta Pharmaceutica Sinica, vol. 36, No. 7, 2000 pp. 532–534.
Li Gang et al., "Found a New Crystal Structure in Nateglinide by X–ray Powder Diffraction," Chinese Journal of Pharmaceutical Analysis, vol. 21, No. 5, 2001, pp. 342–344.

* cited by examiner

Primary Examiner—Rita Desai
Assistant Examiner—Hector M. Reyes
(74) Attorney, Agent, or Firm—Kenyon & Kenyon

(57) ABSTRACT

Provided is a process for preparation of an intermediate in the synthesis of nateglinide. Trans-4-isopropylcyclohexane acid chloride is formed by reacting 4-isopropylcyclohexanecarboxyl acid with thionyl chloride in the presence of an effective amount of an organic amide.

Also provided are processes for preparation of nateglinide by acylation of a suitable salt of D-phenylalanine with trans-4-isopropylcyclohexane acid chloride in both a single and a two phase system, and in water free of a co-solvent.

57 Claims, 3 Drawing Sheets

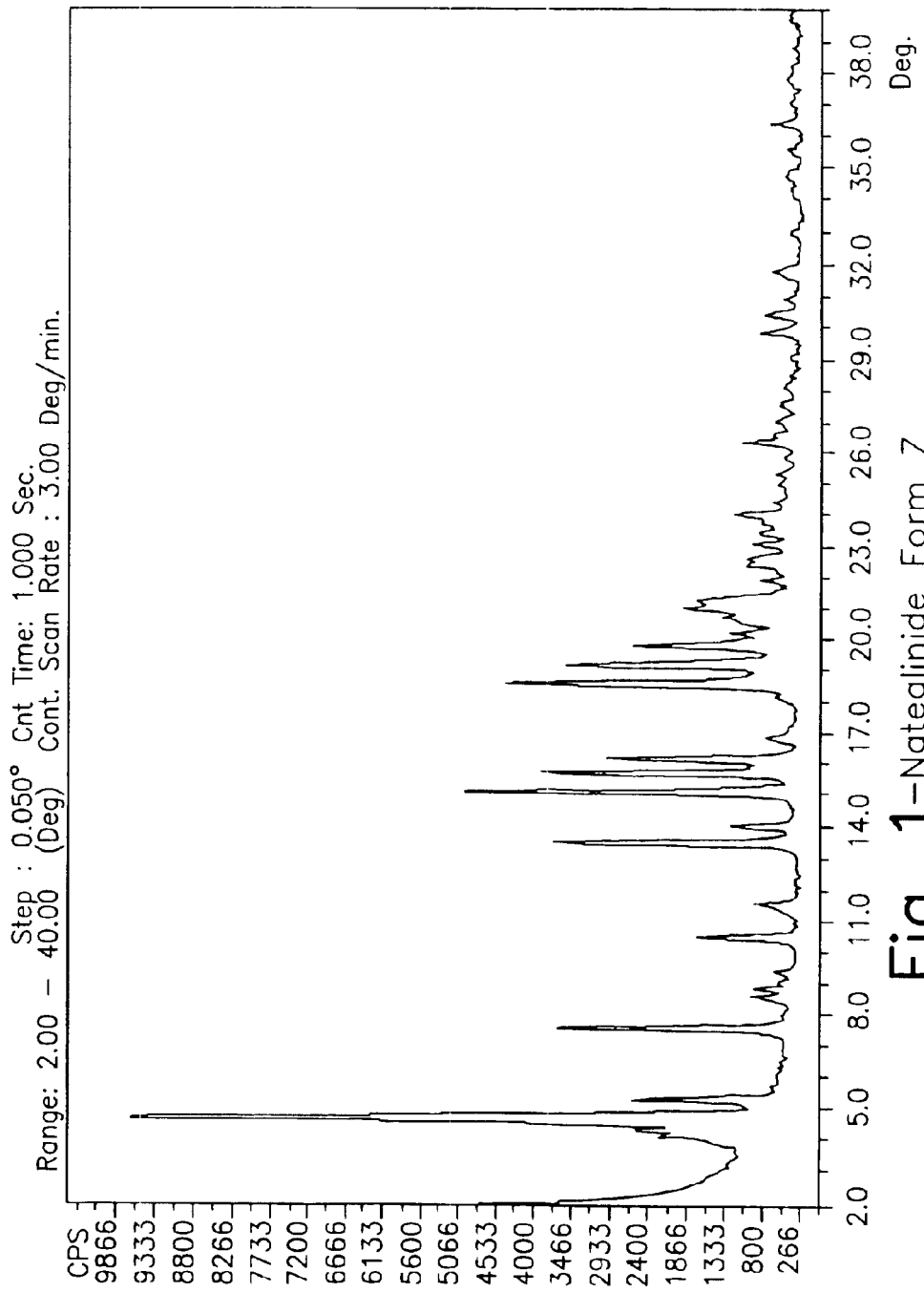

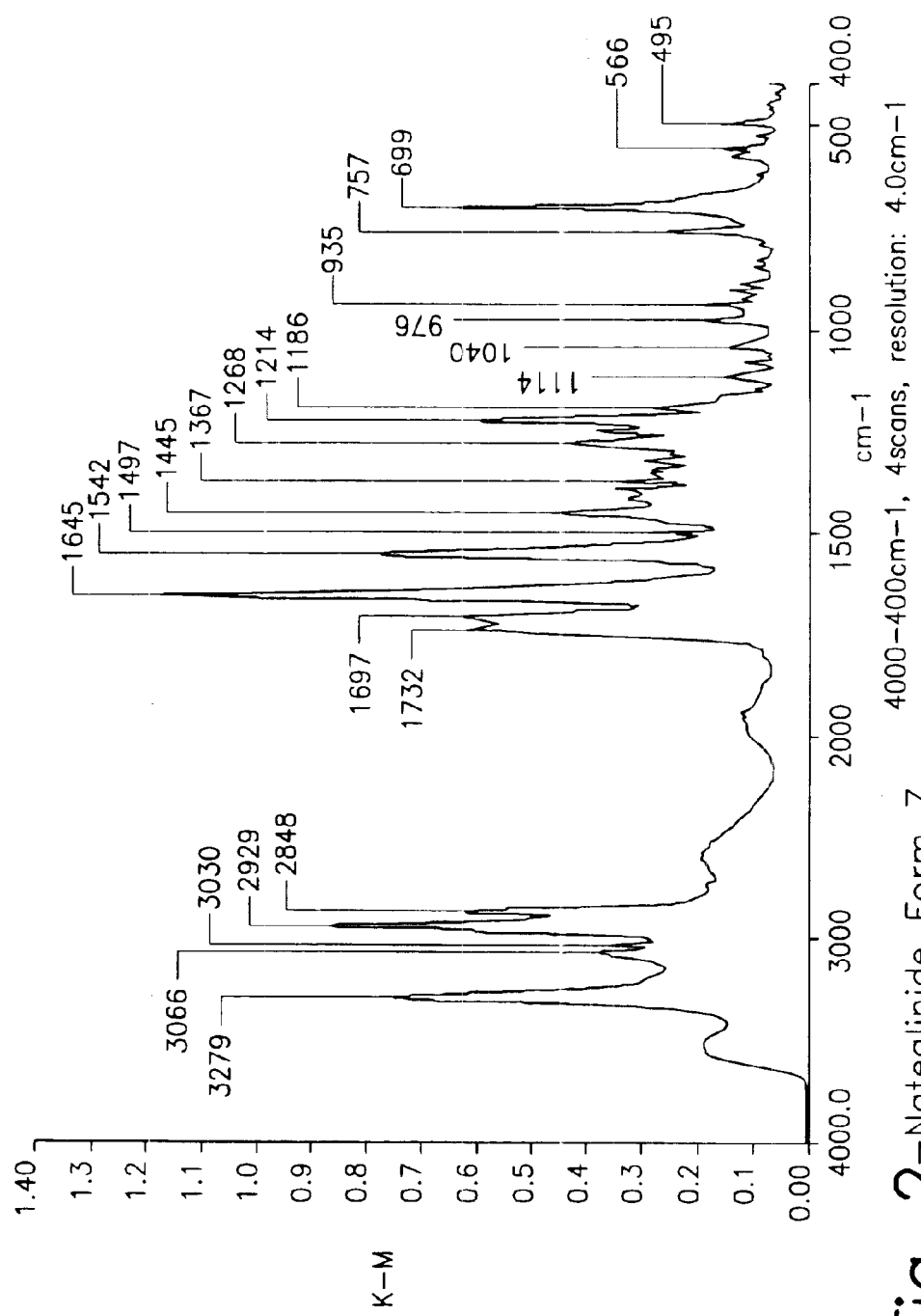
Fig. 2 – Nateglinide Form Z

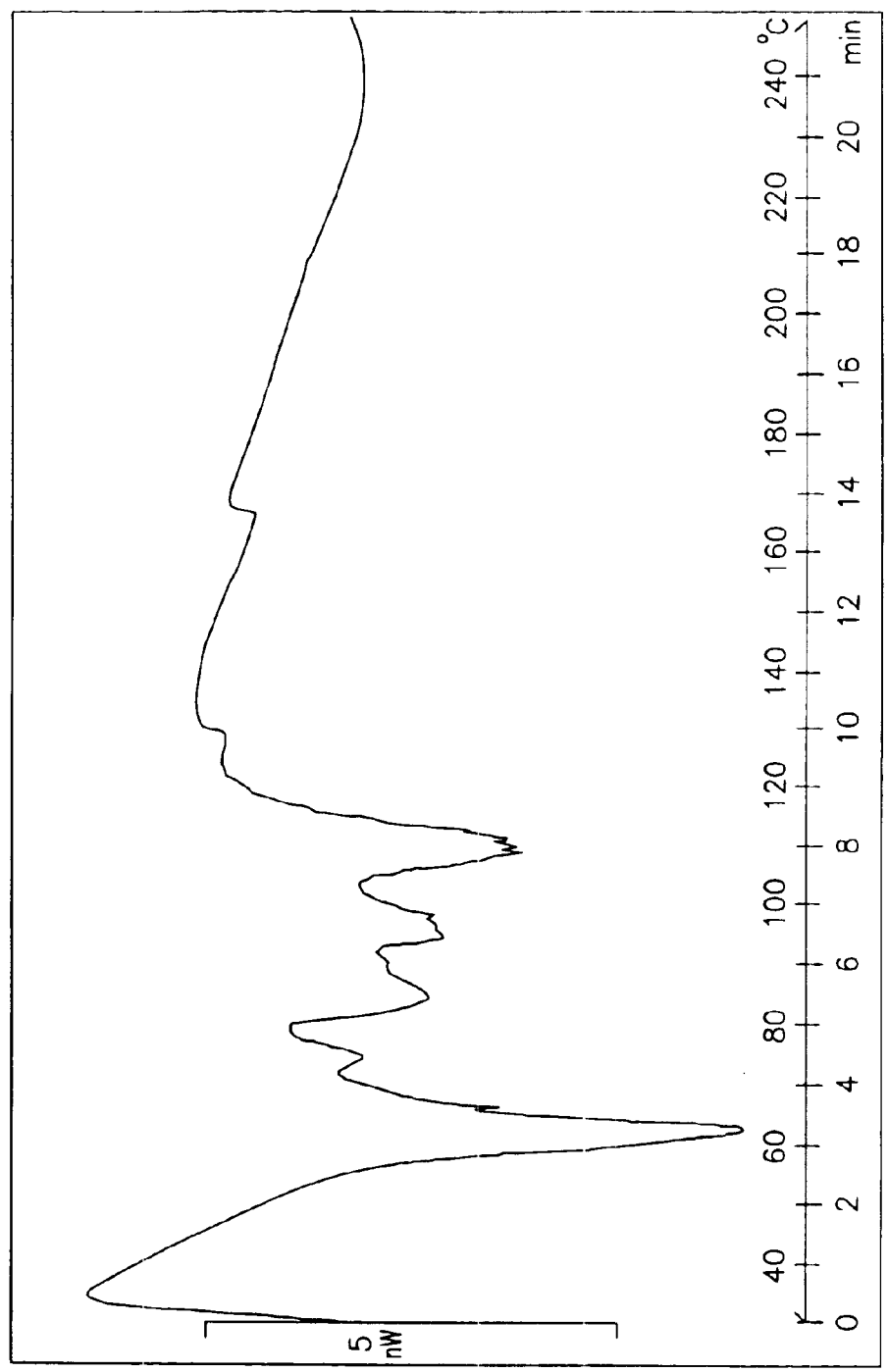
Fig. 3 — Nateglinide Form Z

PROCESS FOR PREPARING NATEGLINIDE AND INTERMEDIATES THEREOF

CROSS-REFERENCE TO RELATED APPLICATIONS

This application claims the benefit under 35 U.S.C. §119 (e) of provisional applications Ser. Nos. 60/393,495 filed Jul. 3, 2002; 60/396,904 filed Jul. 18, 2002; 60/413,622, filed Sep. 25, 2002; 60/414,199, filed Sep. 26, 2002; 60/423,750, filed Nov. 5, 2002; 60/432,093, filed Dec. 10, 2002; 60/432,962, filed Dec. 12, 2002; 60/442,109, filed Jan. 23, 2003; 60/449,791, filed Feb. 24, 2003 and 60/479,016, filed Jun. 16, 2003, the contents of all of which are incorporated herein by reference.

FIELD OF THE INVENTION

The present invention relates to processes for preparing nateglinide and intermediates thereof.

BACKGROUND OF THE INVENTION

Nateglinide, known as (−)-N-(trans-4-isoporpylcyclohexanecarbonyl)-D-Phenylalanine, has the following structure and characteristics:

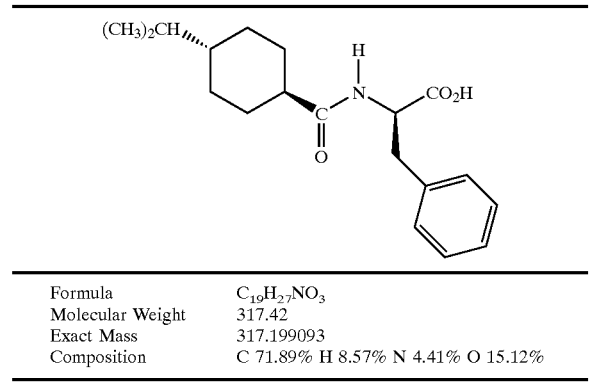

| Formula | $C_{19}H_{27}NO_3$ |
|---|---|
| Molecular Weight | 317.42 |
| Exact Mass | 317.199093 |
| Composition | C 71.89% H 8.57% N 4.41% O 15.12% |

Nateglinide is marketed as STARLIX, which is prescribed as oral tablets having a dosage of 60 mg and 120 mg for the treatment of type II diabetes. STARLIX may be used as monotherapy or in combination with metaformin to stimulate the pancreas to secrete insulin. According to the maker of STARLIX, nateglinide is a white powder that is freely soluble in methanol, ethanol, and chloroform, soluble in ether, sparingly soluble in acetonitrile and octanol, and practically insoluble in water. Metabolites of nateglinide are disclosed in Hiroko Takesada, et al., Bioorg. Med. Chemical, 4(10) 1771–81 (1996).

U.S. Pat. No. 4,816,484 and its subsequent reissue (U.S. Re 34878) disclose nateglinide and a method for its preparation. The process of the '484 patent reacts a D-phenylalanine ester derivative with a DCC derivative of 4-isopropylcyclohexanecarboxylic acid, followed by de-esterification to obtain nateglinide, as illustrated below:

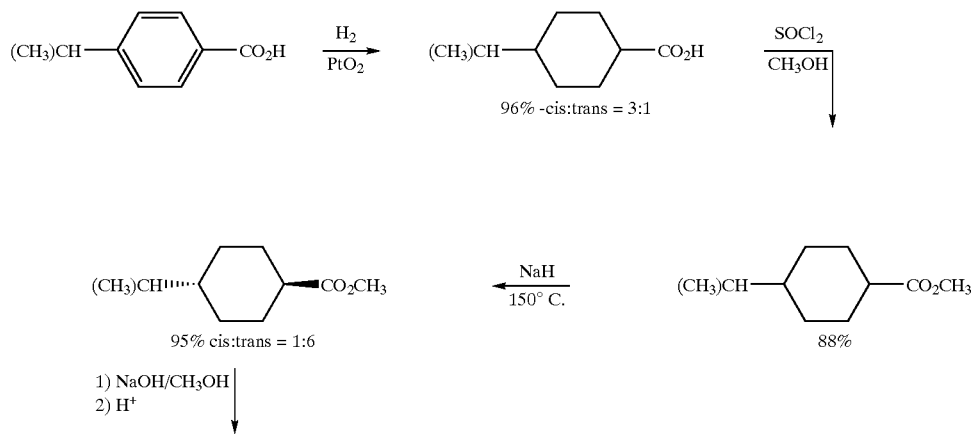

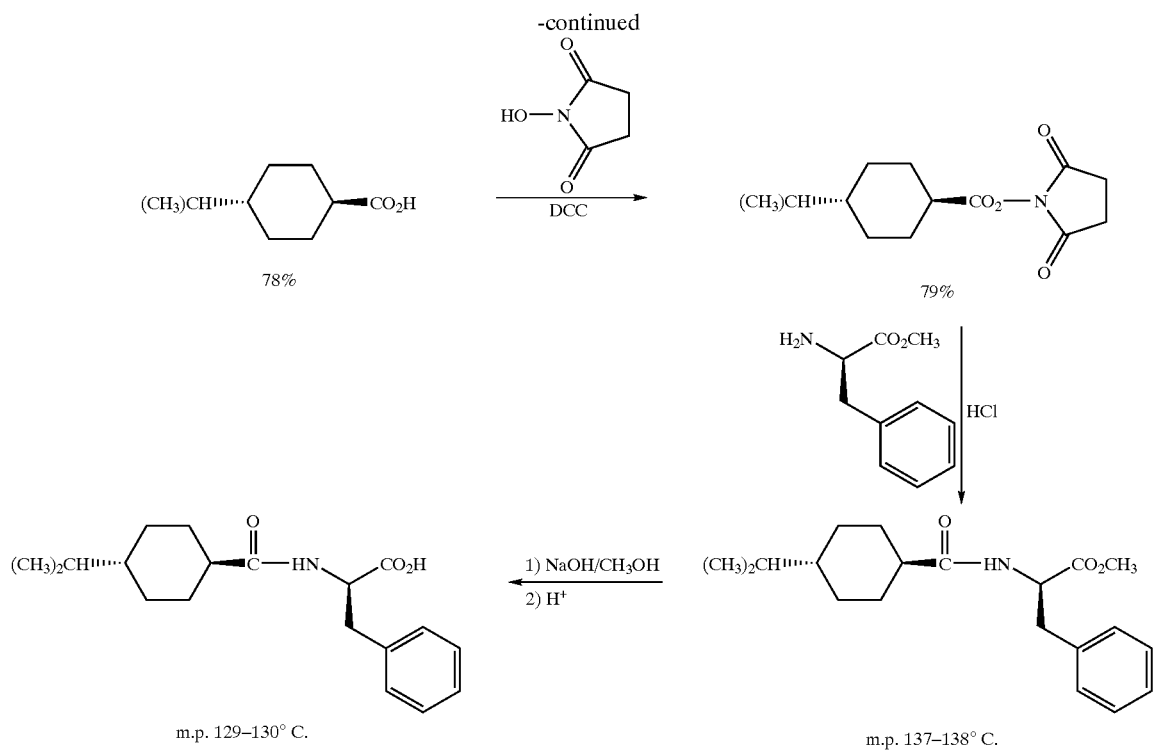

The yield obtained is 65%.

The ester acts as a protecting group, limiting the amount of undesirable cross reactions. The process of U.S. Pat. No. 4,816,484 however may contaminate the final product with the methyl ester since removal of the ester as a protecting group would probably not be complete, leaving at least some minor amounts of the ester as an impurity in the final product. In addition, crystallization from aqueous methanol might result in esterification of the product.

A general problem with preparing nateglidine is the presence of the corresponding undesirable cis isomer during the process, which leads to a final product that is contaminated with the corresponding cis isomer. In order to increase the ratio of the therapeutically effective trans isomer over its corresponding cis isomer, the process of the '484 patent heats a cis-trans mixture of the methyl ester of 4-isopropylcyclohexane carboxylic acid in the presence of sodium hydride. A discussion of U.S. Pat. No. 4,816,484 may be found in Hisashi Shinkai, et. al., J. Med. Chem. 32(7) 1436–1441 (1989).

A Chinese article discloses another reaction scheme for preparing nateglinide, in which the cis to trans ratio of isopropyl cyclohexylcarboxylic acid is decreased by treatment with KOH in methanol at elevated temperatures. Xue-yan Zhu, et. al., Hecheng Huaxue 9(6) 537–540 (2001) (hereinafter "Xue-yan Zhu"). The reaction uses phosphorus pentachloride ("$PCl_5$") to chlorinate isopropylcyclohexane carboxylic acid, to obtain an acid chloride, which is then reacted with D-phenylalanine to obtain nateglinide. The reaction has the following scheme, which may result in contamination of the final product with nateglinide's corresponding cis impurity:

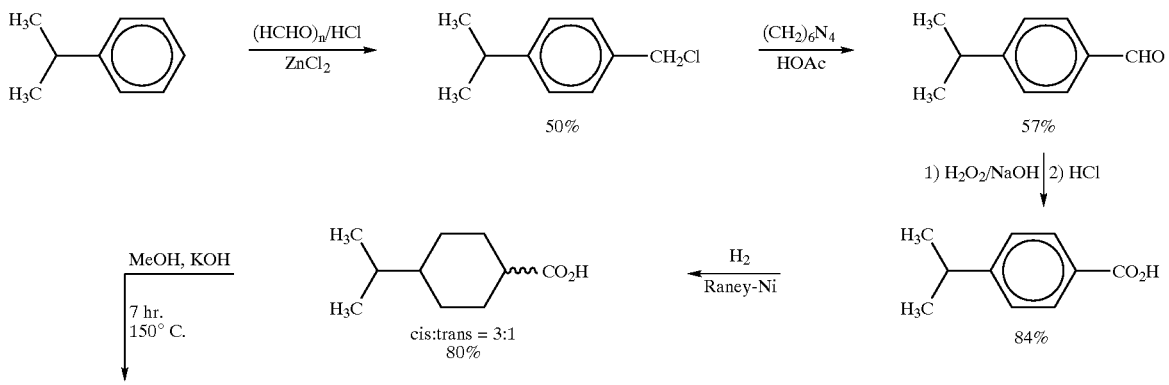

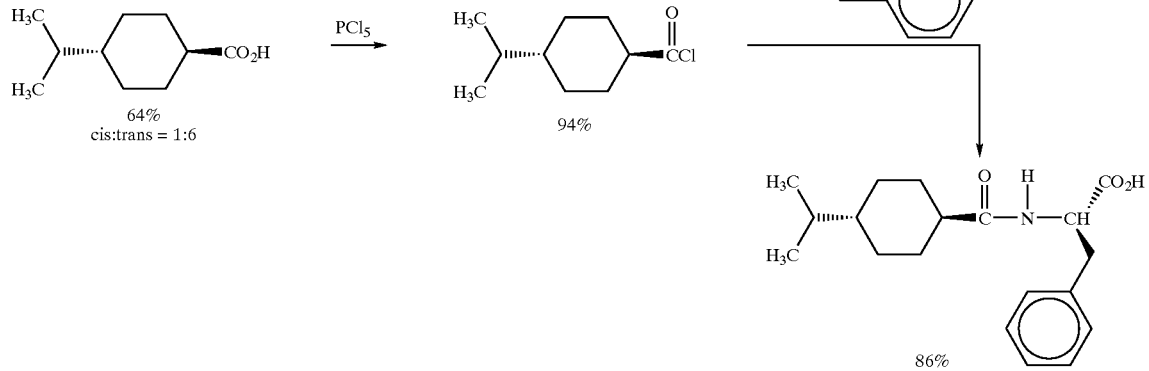

Another article discloses a process for preparing the trans isomer of 4-isopropylcyclohexane carbonyl chloride (syn. of 4-isopropylcyclohexane acid chloride ("IPCHAC") by chlorination of 4-isopropylcyclohexanecarboxylic acid with $PCl_5$ [Jpn. Kokai Tokkyo Kohop (1995) (hereinafter "Kokai")]. Kokai and a Japanese patent, JP 070107899A, disclose that use of thionyl chloride leads to formation of the corresponding cis isomer.

In addition to the above references, nateglinide is also disclosed in U.S. Pat. Nos. 5,463,116 and 5,488,150, and three Japanese publications: WO 02/34254, WO 02/34285 and WO 02/34713. All of these references are incorporated herein by reference.

There is a need in the art for additional processes for preparing nateglinide.

SUMMARY OF THE INVENTION

In one aspect, the present invention provides a process for preparing trans-4-isopropylcyclohexane acid chloride comprising the steps of:
a) combining trans-4-isopropylcyclohexane carboxylic acid with thionyl chloride in the presence of a $C_1$ to a $C_6$ organic amide to obtain trans-4-isopropylcyclohexane acid chloride substantially free of its corresponding cis isomer; and
b) recovering the trans-4-isopropylcyclohexane acid chloride.

In another aspect, the present invention provides a process for preparing nateglinide comprising the steps of:
a) combining trans-4-isopropylcyclohexane carboxylic acid with thionyl chloride in the presence of a $C_1$ to a $C_6$ organic amide to obtain trans-4-isopropylcyclohexane acid chloride substantially free of its corresponding cis isomer; and
b) converting the acid chloride to nateglinide; and
c) recovering the nateglinide.

In another aspect, the present invention provides a process for preparing nateglinide in a two phase system comprising the steps of:
a) preparing an aqueous solution of an alkaline earth or alkali metal salt of D-phenylalanine;
b) combining the aqueous solution with a water immiscible organic solvent containing trans-4-isopropylcyclohexane acid chloride, to form an aqueous and an organic phase, wherein nateglinide forms through reaction between the D-phenylalanine and the trans-4-isopropylcyclohexane acid chloride; and c) recovering the nateglinide.

In another aspect, the present invention provides a process for preparing nateglinide comprising the steps of:
a) preparing an aqueous solution of an alkaline earth or alkali metal salt of D-phenylalanine in water free of a co-solvent;
b) adding trans-4-isopropylcyclohexane acid chloride as a neat reagent to the aqueous solution to form nateglinide; and
c) recovering the nateglinide.

In another aspect the present invention provides a process for preparing nateglinide comprising the steps of:
a) combining a solution of a tri-alkyl amine salt of D-phenylalanine with trans-4-isopropylcyclohexane acid chloride in a $C_1$ to a $C_7$ amide to form nateglinide; and
b) recovering the nateglinide.

BRIEF DESCRIPTION OF THE FIGURES

FIG. 1 is an XRPD pattern of nateglinide Form Z.
FIG. 2 is an FTIR spectrum of nateglinide Form Z.
FIG. 3 is a DSC thermogram of nateglinide Form Z.

DETAILED DESCRIPTION OF THE INVENTION

The present invention provides facile processes for the preparation of nateglinide and its intermediates. In one embodiment, the present invention provides a process for preparing trans-4-isopropylcyclohexane acid chloride, an intermediate in the synthesis of nateglinide, substantially free of the corresponding cis-isomer. As used herein, "substantially free" refers to being undetectable by gas chromatography ("GC"), as carried out under the conditions disclosed in the present invention. Preferably, the amount of cis-4-isopropylcyclohexane acid chloride is less than about 0.1% (wt/wt) compared to the corresponding trans isomer, more preferably less than about 0.05% (wt/wt) and most preferably less than about 0.03% (wt/wt).

The present invention prepares trans-4-isopropylcyclohexane carbonyl chloride (syn. Isopropylcyclohexane acid chloride-("IPCHAC")) by reacting trans-4-isopropylcyclohexanecarboxylic acid with thionyl chloride in the presence of an organic amide. Examples of such organic amides include cyclic and acyclic $C_1$ to $C_6$ amides such as N,N-dimethylacetamide, N-methylpyrrolidone and N,N-dimethylformamide. The amide acts as a catalyst. The reaction between thionyl chloride and trans-isopropylcyclohexane carboxylic acid without catalyst at 70–80° C. affords up to 20% of the cis-isomer. However, in the presence of an organic amide catalyst, the cis-isomer is not formed nor detected in amounts of less than about 0.05% even at elevated temperature (60–80° C.).

In a preferred embodiment, a mixture of N,N-dimethylformamide, thionyl chloride and trans-4-isopropylcyclohexanecarboxylic acid is prepared. The mixture may be prepared in a suitable aprotic organic solvent, or preferably with a neat reagent. Examples of such solvents include $C_5$ to $C_{12}$ aliphatic and aromatic hydrocarbons (including fluorinated and chlorinated), ethers, esters, among others.

The trans intermediate used, trans-4-isopropylcyclohexane carboxylic acid, is preferably substantially free of the corresponding cis isomer, i.e., less than about 0.2% of the corresponding cis isomer. The trans-4-isopropylcyclohexanecarboxylic acid may be prepared according to the methods known in the art, such as example 31 of U.S. Pat. No. 4,816,484 (Re 34,878), where a process for the preparation of t-4-isopropylcyclohexanecarboxylic acid by the hydrogenation of cumic acid is disclosed. A preferred re-crystallization solvent system for the trans-4-isopropylcyclohexane carboxylic acid is a mixture of methanol and water.

The reaction is preferably carried out with from about 1 to about 5 acid equivalents of thionyl chloride and an effective amount of amide preferably from about 0.05% to about 10% wt/wt (amide/acid). The reaction may be carried out at a temperature of from about minus 10° C. to about 60° C., with about room temperature being preferred.

After preparing the mixture of 4-isopropylcyclohexanecarboxylic acid, thionyl chloride and the amide, the mixture is preferably stirred and allowed to sit for a few hours (about 1 to about 5 hours) for the carboxylic acid to be chlorinated. The chlorinated product (IPCHAC) is then recovered, such as by separation from the solvent or other volatiles, including the neat reagent. In a preferred embodiment, the pressure is reduced, and the temperature is raised slightly, to about 40° C., to evaporate the solvent or other volatiles. After evaporation, the product, trans-4-isopropylcyclohexane acid chloride (liquid at room temperature), is obtained, substantially free of the corresponding cis isomer. The purity of the product from this process is preferably at least about 95% as measured by HPLC, and the cis-isomer is preferably undetectable by GC.

The trans-4-isopropylcyclohexane acid chloride prepared may then be used to prepare nateglinide substantially free of the corresponding cis isomer. The processes of the present invention prepare nateglinide by acylation of a salt of D-phenylalanine with trans-4-isopropylcyclohexane acid chloride.

Preferred salts of phenylalanine for acylation are the sodium and potassium salts. Other salts of alkali metals such as that of lithium may also be used. In addition to alkali metals, salts of alkaline earth metals such as magnesium and calcium may also be used. Another group of salts that may be used are those of $C_1$ to $C_7$ tri-alkyl amines, such as tri-ethyl amine. One of skill in the art would appreciate that a suitable base such as sodium/potassium carbonate or hydroxide may be added to phenylalanine to obtain the desired salt.

In one embodiment, the present invention provides for preparation of nateglinide by use of a two phase system, i.e., an aqueous phase and an organic water immiscible phase. Examples of water immiscible solvents in the organic phase include aromatic hydrocarbons and saturated hydrocarbons, more preferably a $C_5$ to a $C_{12}$ hydrocarbon. Preferred solvents include toluene and heptane. Water immiscible esters and ketones, such as ethyl acetate, may also be used.

In one embodiment of the two phase system, a solution of trans-4-isopropylcyclohexane acid chloride in a water immiscible organic solvent and an aqueous solution of sodium/potassium salt of D-phenylalanine is added to the reaction medium, resulting in a two phase system. The temperature of the reaction is maintained from about 0° C. to about 60° C., more preferably about 40° C. to about 50° C. As a result, nateglinide forms between the two phases.

The pH of the reaction is preferably above about 8. A sufficient amount of a base such as sodium hydroxide is used to keep the pH above about 8, preferably from about 12 to about 14. Under basic conditions, after synthesis of nateglinide, a salt or anion of nateglidine, preferably the sodium salt, forms and accumulates in the aqueous phase. It is believed the yield increases as the pH increases above about 8 probably due to its inhibition of side reactions.

Nateglinide is then recovered from the aqueous phase, preferably by acidification. In the acid form, nateglinide readily dissolves in toluene or ethyl acetate. Acidification of an aqueous solution of nateglinide results in precipitation of nateglinide. While the sodium salt of nateglidine is soluble in water, nateglidine itself is insoluble in water. Hence acidification will neutralize the salt, resulting in precipitation. The pH of the aqueous phase is preferably adjusted to from about 1 to about 5, more preferably from about 2 to about 3. Acids such as hydrochloric acid, sulfuric acid, formic acid, acetic acid and phosphoric acid may be used to adjust the pH.

After acidification, the product precipitates. Precipitation is preferably carried out at room temperature, though other temperatures may also be used. The precipitate may be separated by techniques well known in the art, such as filtration, preferably at room temperature. The product may be washed with water or an organic solvent, and preferably dried. The product may be dried, preferably from about 40° C. to about 120° C., most preferably about 100° C. under reduced pressure.

In one embodiment, the nateglinide is moved to the water immiscible organic solvent, such as ethyl acetate and toluene. The organic solvent extracts the nateglinide, preferably at a pH where the nateglinide is neutral (preferably less than about 4, more preferably from about 1 to about 2), resulting in nateglinide moving substantially to the organic phase. Nateglinide may then be recovered from the organic phase by conventional techniques. In one embodiment, the organic phase is concentrated, preferably by evaporation under reduced pressure, to obtain nateglinide.

In another embodiment, the present invention provides a process for preparing nateglinide by using only an aqueous solvent and adding isopropylcyclohexane acid chloride as a neat reagent, i.e., acylation may be carried in an aqueous solvent system in the absence of a water immiscible organic solvent. The neat reagent may contain negligible amounts of N,N-dimethyl formamide ("DMF"), from about 0.05% to about 8%, preferably less than about 5%, more preferably about 1%, weight of DMF compared to the weight of the neat reagent. The pH of the reaction is preferably above about 8, more preferably at least about 12.

This embodiment is similar to those described above, except a water immiscible organic solvent is not at least initially added to the aqueous solution containing salt of D-phenylalanine. Rather, 4-isopropylcyclohexane acid chloride is added as a neat reagent in slight excess. Preferred solvents for the solution are dipolar aprotic solvents such as acetonitrile and lower ketones such as acetone in a mixture with water. Use of water without a co-solvent is also preferred. The temperature of the reaction is preferably kept from about −5° C. to about 60° C., more preferably from about 40° C. to about 50° C.

After addition of the 4-isopropylcyclohexane acid chloride, nateglinide is recovered from the reaction mixture. Nateglinide may also be recovered by precipitation or from an organic solvent/phase as discussed above.

The preparation of nateglinide often results in an undesirable product, referred to herein as a dimer. A possible reaction scheme for the dimer is illustrated in the following diagram:

The term co-solvent refers to a second solvent used in combination with a first solvent in such amounts to substantially change a property of the solvent, such as solubility. Impurities and traces of a solvent are not co-solvents. Hence, water free of or without co-solvent may include a small amount of other solvents, but preferably less than about 5% v/v, and most preferably less than about 1% v/v of other solvents.

In another embodiment, a tri-alkyl amine salt of D-phenylalanine is reacted with trans-4-isopropylcyclohexane acid chloride in a cyclic or a non-cyclic $C_1$ to a $C_6$ amide as a solvent. Examples of such amides include dimethyl formamide, dimethyl acetamide ("DMA") and N-methyl pyrolidone. In one embodiment, tri-alkyl salts of D-phenylalanine are reacted with trans-4-isopropylcyclohexane acid chloride in DMF. The resulting product may then be recovered as described above. Preferred tri-alkyl amines are $C_1$ to $C_7$ amines, with tri-ethyl amine being the most preferred.

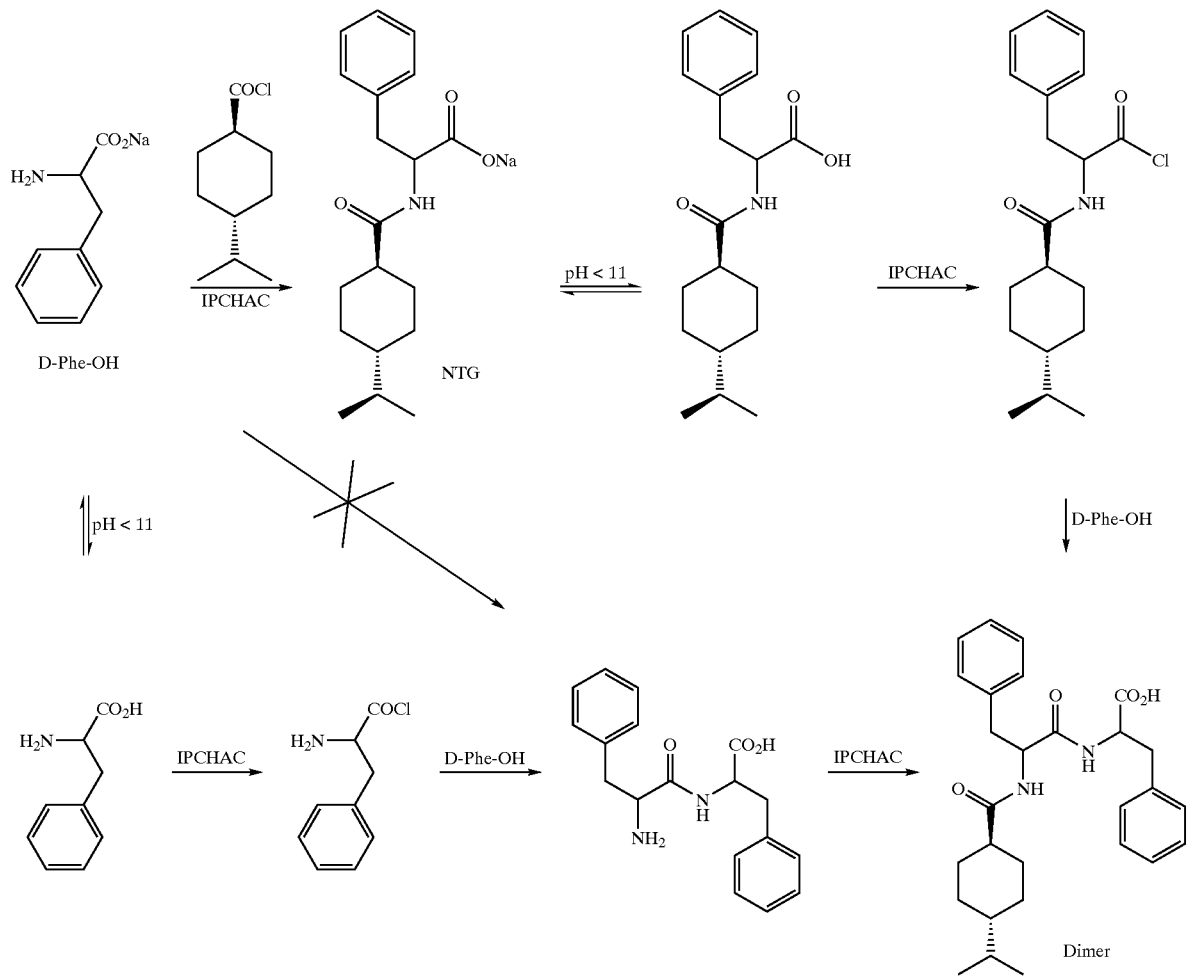

When water is used, without a co-solvent, preferably in conjunction with a strong base such as sodium or potassium hydroxide, the product is substantially free of the undesirable dimer, i.e., the dimer is not detectable by GC. The amount of the dimer in the final product in this embodiment is preferably from about 0.04% to about 0.1% wt/wt of the dimer to nateglinide. As used herein, a strong base refers to a base that reacts essentially completely to give hydroxide ions when put in water.

One of skill in the art would appreciate that the nateglinide prepared by the processes of the present invention may be crystallized/recrystallized as various polymorphic forms of nateglinide. For example, U.S. Pat. Nos. 5,463,116 and 5,488,150, both incorporated herein by reference, disclose two crystal forms of nateglinide, designated B-type and H-type, and processes for their preparation. Another crystalline form of nateglinide designated Type-S is disclosed in two Chinese articles: ACTA Pharm. Sinica 2001, 36(7), 532–34 and Yaowu Fenxi Zazhi, 2001, 21(5), 342–44. The nateglinide prepared by the present invention may be re-crystallized from a mixture of lower alcohol such as methanol or ethanol with water. Additional polymorphic forms and processes for their preparation are disclosed in U.S. provisional application Nos. 60/396,904, 60/413,622, 60/432,962, 60/442,109, 60/449,791 and 60/479,016, filed Jun. 16, 2003. Example 2 and 9 of the present invention results in nateglinide Form Z disclosed in the above applications.

A hydrate of nateglinide, Form Z, has a water content of about 10 to about 50%, more preferably about 10% to about 40%, and most preferably from about 15% to about 25%, measured either by the Karl Fischer method or LOD. Nateglinide Form Z has an XRPD pattern with peaks at 4.7, 5.3, 13.5, 13.9, 15.1, 15.7, 16.1, 18.7, 19.5, 21.5±0.2 degrees 2θ (FIG. 1). The more characteristic peaks are observed at 4.7, 5.3, 15.1, 15.7 and 16.1±0.2 degrees 2θ. Form Z is also characterized by a FTIR spectrum (FIG. 2) with peaks at about 699, 1542, 1645, 1697, 2848, 2864, 2929, 3279 and 3504 $cm^{-1}$. The more characteristic peaks are observed at about 1645, 1697, 3279 and 3504 $cm^{-1}$.

Nateglinide Form Z is generally prepared by acidification of a solution of an alkali metal or alkaline earth metal salt of nateglinide in an aqueous solvent. Preferred solvent is water free of a co-solvent. Preferred salts are sodium and potassium salts, with the sodium salt being most preferred. Before acidification, the solution preferably has a pH of above about 8, while after acidification, the pH is preferable from about 1 to about 5, most preferably from about 2 to about 5. Acidification results in precipitation of nateglinide, which may be recovered by techniques well known in the art, such as filtration.

Even thought Example 2 of the present invention results in nateglinide Form Z, the processes of the present invention may be manipulated to obtain other polymorphic forms of nateglinide. The other polymorphic forms may be obtained either directly (such as from a solution) or through another polymorphic form (such as by recrystallization).

Nateglinide of defined particle size may be produced by known methods of particle size reduction starting with crystals, powder aggregates and course powder of either crystalline or amorphous nateglidine. The principal operations of conventional size reduction are milling of a feedstock material and sorting of the milled material by size.

A fluid energy mill, or micronizer, is an especially preferred type of mill for its ability to produce particles of small size in a narrow size distribution. As those skilled in the art are aware, micronizers use the kinetic energy of collision between particles suspended in a rapidly moving fluid (typically air) stream to cleave the particles. An air jet mill is a preferred fluid energy mill. The suspended particles are injected under pressure into a recirculating particle stream. Smaller particles are carried aloft inside the mill and swept into a vent connected to a particle size classifier such as a cyclone. The feedstock is preferably first milled to about 150 to about 850 µm, which may be done using a conventional ball, roller, or hammer mill.

Pharmaceutical compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Pharmaceutical compositions of the present invention contain nateglidine substantially free of the corresponding cis-isomer. In addition to the active ingredient(s), the pharmaceutical compositions of the present invention may contain one or more excipients. Selection of excipients and the amounts to use may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

The active ingredient and excipients may be formulated into compositions and dosage forms according to methods known in the art. The dosage and formulation of STARLIX may be used as a guidance. The dosage used is preferably from about 30 to about 240 mg of nateglinide, more preferably from about 60 to about 120 mg of nateglidine.

The pharmaceutical compositions of the present invention, preferably in the form of a coated tablet, are administered from about 10 minutes to about 1 hours prior to a meal, more preferably about 15 minutes before each meal. The dose is not taken if the meal is skipped. The pharmaceutical compositions may also be used in combination with metaformin.

Instrumentation Used

Instrument: GC-HP® model 5890

Oven: Initial temp 80° C., hold for 2 min, raise to 100° C. at 10° C./min, then raise to 300° C. at 20° C./min Injector: 250° C. (split mode, 1:50)

Detector: 300° C.

Column: Rtx-1, 15 m, 0.25 mm ID, 0.25 mm film thickness

Injection amount: 1 ml

Instrument: HPLC-HP® model 1050 equipped with a Jasco UVIDEC-100V detector

Column: Ace 5 C18 A6667 column (250×4.6 mm)

Temperature: room temperature

Loop: 20 ml

Injection volume: 40 ml

Flow rate: 1.5 ml/min

Wave length: 214 nm

Solvent A: acetonitrile

Solvent B: water containing TFA till pH 2.5

The gradient profile: solvent B 50% 17 min, 0% 21 min, 0% 31 min, 50% 35 min.

The purity determinations are expressed as area percentages of HPLC.

X-Ray diffraction was performed on X-Ray powder diffractometer, Scintag®, variable goniometer, Cu-tube, solid state detector. Sample holder: A round standard aluminum sample holder with round zero background quartz plate. The sample was put on the sample holder and immediately analyzed as is. Scanning parameters: Range: 2–40 deg 2θ, Continuos Scan, Rate: 3 deg./min.

DSC821$^e$ Mettler Toledo®, Sample weight: 3–5 mg, Heating rate: 10° C./min, Number of holes in the crucible: 3

Perkin-Elmer®, Spectrum One FTIR spectrometer, Range: 4000–400 cm-1, No. of scans: 16, resolution: 4.0 cm-1, DRIFT technique.

EXAMPLES

Some of the following examples use neat IPCHAC or trans-4-Isopropylcyclohexane carboxylic acid, which contain from about 0.05 to about 8% DMF (weight/weight) of DMF to IPCHAC or the carboxylic acid. The carboxylic acid in Example 1 contains about 1% DMF weight to weight of DMF to the carboxylic acid. The DMF is not considered a co-solvent.

Example 1

Preparation of IPCHAC by Chlorination in the Presence of an Amide

N,N-dimethylformamide (0.1 ml), followed by neat trans-4-isopropylcyclohexanecarboxylic acid (9.92 g) [containing a level of cis isomer of less than 0.1%] were added to thionyl chloride (8.32 g) at room temperature. The mixture was stirred for 2 h at room temperature and volatiles were removed under reduced pressure in a 40° C. bath to afford 10.39 g of the desired product, trans-4-isopropylcyclohexane acid chloride, with a purity of 97%, as a colorless liquid. No cis-isomer was detected by GC. Yield: 96%.

Example 2

Preparation of IPCHAC by Chlorination in the Presence of an Amide in Ethyl Acetate N,N-dimethylformamide (0.1 g) was added to a mixture of trans-4-isopropylcyclohexanecarboxylic acid (20.0 g) in ethyl acetate (8 ml). The mixture was heated to 40° C. and thionyl chloride (16.1 g) was gradually added for 1 hour. The mixture was stirred for 1 h at 40° C. and volatiles were removed under reduced pressure in a 40° C. bath to afford 22.43 g of the desired product, trans-4-isopropylcyclohexane acid chloride, with a purity of 98%, as a colorless liquid. No cis-isomer was detected by GC. Yield 99%.

Example 3

Preparation of IPCHAC by Chlorination in the Presence of an Amide

N,N-dimethylformamide (0.63 g) was added to a neat trans-4-isopropylcyclohexanecarboxylic acid (250 g) placed into a two liter reactor. The mixture was cooled to 18° C. and thionyl chloride (189.8 g) was gradually added for 15 minutes. The mixture was stirred for 1 h, keeping the temperature around 15° C. to afford a clear solution. Next part of trans-4-isopropylcyclohexanecarboxylic acid (250 g), followed by N,N-dimethylformamide (0.63 g) were introduced into the reactor. Additional amount of thionyl chloride (189.8 g) was added dropwise for 15 min. The mixture was stirred for 1 h, keeping the temperature around 15° C. to afford a clear solution of the crude desired product, which was directly used for the preparation of nateglinide. No cis-isomer was detected by GC.

Example 4

Preparation of IPCHAC by Chlorination in the Presence of an Amide and Heptane

N,N-dimethylformamide (0.2 g) was added to a mixture of trans-4-isopropylcyclohexanecarboxylic acid (39.5 g) in heptane (25 ml). The mixture was heated to 40° C. and thionyl chloride (32.6 g) was gradually added for 1 h. The mixture was stirred for 1 h at 40–45° C. and volatiles were removed under reduced pressure in a 40° C. bath to afford 58.52 g of a heptane solution of the desired product, trans-4-isopropylcyclohexane acid chloride, as a colorless liquid containing approximately 0.28% of the starting trans-4-isopropylcyclohexanecarboxylic acid. No cis-isomer was detected by GC. Yield 95%. The solution was directly used for the preparation of nateglinide.

Example 5

Preparation of IPCHAC by Chlorination in the Presence of an Amide

N-Methylpyrolidone (0.11 g), followed by a neat trans-4-isopropylcyclohexanecarboxylic acid (9.92 g) were added to thionyl chloride (8.33 g), at room temperature. The mixture was stirred for 2.5 h at room temperature and volatiles were removed under reduced pressure in a 4° C. bath to afford 10.97 g of the desired product, trans-4-isopropylcyclohexane acid chloride. No cis-isomer was detected by GC. Yield 99%.

Example 6

Preparation of Nateglinide with a Two Phase System with Toluene/Water

D-phenylalanine (7.74 g) was dissolved in a solution of sodium hydroxide (2.1 g) in water (100 ml). The clear aqueous solution was covered with toluene (25 ml) and cooled to 10° C. A solution of trans-4-isopropylcyclohexane acid chloride 10.39 g in toluene (50 ml) and 10% sodium hydroxide solution were simultaneously added to the two phase mixture, maintaining the temperature around 10° C. and pH>8. The reaction mixture was allowed to warm to room temperature and stirred for 2 hours. The phases were separated. The aqueous phase was extracted with toluene (30 ml). The organic phases were combined, washed with water (30 ml) and discarded. The aqueous phases were combined and the pH was adjusted to 2–3 with 10% hydrochloric acid. The precipitated solid was filtered off, washed with water (20 ml) and dried at 60° C. under reduced pressure to afford 10.15 g of the desired product. Yield 61%.

Example 7

Preparation of Nateglinide with a Neat Reagent in a Water/Acetone Mixture

D-Phenylalanine (7.71 g, 0.0462 mol) was dissolved in a 10% NaOH (65 ml) solution and acetone (70 ml) was added, and the reaction mixture was cooled to 15° C. Neat isopropylcyclohexyl acid chloride (11.13 g, 1.25 equivalent) was added to the solution over 6 minutes while stirring and maintaining the temperature of 17–21 ° C. The rest of the isopropylcyclohexyl acid chloride in the dropping funnel was washed with acetone (~10 ml) and added to the reaction solution. The reaction mixture was allowed to warm to room temperature (25–28° C.). Precipitation occurred and stirring became difficult. After pH was adjusted to >11, the reaction mixture was gradually transformed into a clear solution. The mixture was stirred for 1 hour and was made acidic with 10% HCl (22 ml, pH 1–2). The organic phase was separated and volatiles were removed under reduced pressure at ~60° C. to afford 16.32 g of a crude product, as a white solid. The yield was 87%.

Example 8

Preparation of Nateglinide with a Neat Reagent in a Water/Acetone Mixture

D-Phenylalanine (7.73 g, 0.0462 mol) was dissolved in a 10% NaOH solution (70 ml), acetone (70 ml) was added, and the reaction mixture was cooled to 15 °C. Neat isopropylcyclohexane acid chloride (11.19 g, 1.25 equivalent) was added to the solution over 6 minutes while stirring and maintaining the temperature 15–23° C. The rest in the dropping was funnel washed with acetone (~10 ml) and added to the reaction solution. The reaction mixture was allowed to warm to room temperature (25–28 °C.). Precipitation occurred and stirring became difficult. After pH was >11, the mixture was stirred for 1 h and was made acidic with 10% HCl (35 ml, pH 1–2). The mixture was partitioned between water (50 ml) and EA (90 ml). The organic phase was separated. The aqueous phase was additionally extracted with EA (90 ml). The organic phases were combined, dried with sodium sulfate, filtered and evaporated to afford 19.61 g of a crude product as a white solid. The solid was dried in a vacuum oven at 65–70° C. to afford 15.26 g of a white solid. The yield was 80%.

Example 9

Preparation of Nateglinide with a Neat Reagent in a Water Free of a Co-solvent D-Phenylalanine (Phe-OH, 7.73 g) was treated with 3.5% NaOH (185 ml, 3.5 equivalents), at room temperature to afford a clear solution of the corresponding Na-salt. Neat trans-4-isopropylcyclohexane acid chloride (IPCHAC, 9.02 g, 1.01 equivalent) was added to the solution of phenylalanine obtained above, over 3 minutes, while stirring at room temperature. The resulting mixture was stirred for 1 hour, and was treated with 10% HCl (32 ml) to adjust the pH to 3, while stirring. The mixture was stirred for 1 hour, and filtered. The solid was washed with water (200 ml) and sucked well to afford 33.3 g of the moist product, which lost weight after drying at 78° C./2.2 mbar. Assay 98.4%, purity>99%, yield 86%. Form Z was obtained as polymorphic form. [The minimal values of purity and yield are over 99% and 80% respectively.]

Example 10

Preparation of Nateglinide with a Two Phase System of Ethyl Acetate/Water

D-phenylalanine (7.74 g) was dissolved in a solution of sodium hydroxide (2.1 g) in water (25 ml). The clear aqueous solution was covered with ethyl acetate (50 ml) and cooled to 10° C. A solution of trans-4-isopropylcyclohexane acid chloride (10.39 g) in ethyl acetate (15ml) and 10% sodium hydroxide solution were simultaneously added to the two phase mixture, maintaining the temperature around 10° C. and pH>8. The reaction mixture was allowed to warm to room temperature and stirred for 2 h. Water (30 ml) was added and the phases were separated. The aqueous phase was extracted with ethyl acetate (25 ml). The organic phases were combined, washed with water (25 ml) and discarded. The aqueous phases were combined and the pH was adjusted to 2–3 with 10% hydrochloric acid. The precipitated solid was filtered off, washed with water (20 ml) and dried at 60° C. under reduced pressure to afford 9.54 g of the desired product. Yield 60%.

Example 11

Preparation of Nateglinide with a Two Phase System of Ethyl Acetate/Water

A mixture of $NaHCO_3$ (19.37 g), D-phenylalanine (7.72 g) and water (30 ml) was stirred at 50° C. till the cessation of the gas evaluation. The clear aqueous solution was covered with ethyl acetate (25 ml). A solution of trans-4-isopropylcyclohexane acid chloride (11.33 g) in EA (25 ml) was added to the hot mixture for 1 h. The reaction mixture was stirred for 2 h at 50° C. (pH was >7 whole time of the reaction). The two phase reaction mixture was diluted with water (150 ml) and covered with EA (125 ml). The pH was adjusted to 1 with 10% hydrochloric acid. The organic phase was separated and the aqueous phase was extracted with EA (100 ml). The organic extracts were combined, dried with anhydrous sodium sulfate, filtered, and evaporated to afford 17.45 g of a crude product as a white solid. The yield was 90%.

Example 12

Preparation of Nateglinide with a Neat Reagent in Water

D-Phenylalanine (30.92 g) was treated with 10% KOH (360 ml, 3.5 equivalents), at room temperature to afford a clear solution of the corresponding K-salt. The solution was cooled to 10° C. Neat trans-4-isopropylcyclohexane acid chloride (IPCHAC, 35.92 g, 1.01 equivalents) was added to the solution, over 3 min, while stirring at 10–12° C. A partial precipitation occurred in 2–3 minutes. The mixture was stirred for 1 h and was treated with 10% HCl (53 ml) to adjust pH to 1, under stirring, resulting in complete precipitation. The mixture was allowed to warm to room temperature and stirred for 1 h and filtered. The solid was washed with water (200 ml) and sucked well to afford 145 g of the moist product, which lost in weight after drying at 78° C./2.2 mbar. Assay 88%, purity >99%. The yield was 76%.

Example 13

Preparation of Nateglinide in a Mixture of Water and Acetonitrile with a Weak Base A mixture of $NaHCO_3$ (18.63 g), D-phenylalanine (7.61 g), acetonitrile (75 ml), and water (30 ml) was stirred at 20° C. until the cessation of gas evolution. Ethyl acetate (25 ml) was added to the clear solution. A solution of trans-4-isopropylcyclohexaneacid chloride (10.9 g) in acetonitrile (30 ml) was added to the mixture for 1 h, at room temperature. The reaction mixture was stirred for an additional hour (pH was >9) and evaporated. The residue was partitioned between water (200 ml) and ethyl acetate (100 ml). The organic phase was separated and the aqueous phase was extracted with ethyl acetate (2×50 ml). The aqueous phase was treated with 10% HCl (75 ml) to adjust pH to 1, under stirring. The mixture was extracted with ethyl acetate (2×50 ml). The organic extracts were combined, dried with anhydrous sodium sulfate, filtered, and evaporated to afford 12.61 g of a crude product as a white solid. The yield was 50%.

Example 14

Preparation of Nateglinide in an Amide with a Weak Base

D-phenylalanine (7.71 g) and triethylamine (19 ml) were simultaneously added to a solution of trans-4-isopropylcyclohexaneacid chloride (7.93 g) in N,N-dimethylformamide (21 ml), maintaining the temperature around 40° C. and pH>10. The reaction mixture was stirred for 1 hour, diluted with water (100 ml) and covered with ethyl acetate (100 ml). The pH was adjusted to 1 with 10% hydrochloric acid. The organic phase was separated and the aqueous phase was extracted with ethyl acetate (2×100 ml). The organic extracts were combined and evaporated to afford 15.0 g of a crude product as a white solid. The yield was 41%.

Example 15

Preparation of Nateglinide with a Neat Reagent in Water

D-Phenylalanine (83.5 g) was added to a solution of sodium hydroxide (56.35 g) in water (1550 ml), heated to 45° C. and stirred for 5 min to afford a clear solution. A neat trans-4-isopropylcyclohexaneacid chloride (96.68 g), containing<0.1% cis-isomer was added for 10 min and the reaction mixture was stirred for 30 min at 45–50° C. Ethyl acetate (360 ml) was introduced and pH 1 was adjusted by a 66% sulfuric acid (84.07 g). The mixture was stirred for 15 min at 48° C. and the aqueous phase was separated and discarded. The hot (40–45° C.) organic phase was washed twice with water (150 ml) at 48° C., under stirring. The aqueous phases were separated and discarded. The first portion of hot heptane (48° C., 400 ml) was added to the hot solution and the mixture was stirred for 40 min at 48° C. The mixture was cooled to 31 ° C. and seeded to promote the crystallization. The residue of warm heptane (31 ° C., 740 ml, total 1050 ml) was added for 10 min. The mixture was slowly cooled to 10° C. and stirred for 1 h. The solid was filtered off and washed with a cold (−5° C.) mixture of ethyl acetate and heptane (1:3, 240 ml) to afford 228.04 g of a wet (45%) product. Yield 79%.

The wet product was re-crystallized from a mixture of ethyl acetate and heptane (1.3:1, total 1110 ml) and dried for 2 h at 100° C. to afford the desired product, nateglinide, as a white solid with purity>99.7%. Yield 63%.

Having thus described the invention with reference to particular preferred embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

What is claimed is:

1. A process for preparing trans-4-isopropylcyclohexane acid chloride comprising the steps of:
   a) combining trans-4-isopropylcyclohexane carboxylic acid with thionyl chloride in the presence of a $C_1$ to a $C_6$ organic amide to obtain trans-4-isopropylcyclohexane acid chloride substantially free of its corresponding cis isomer; and
   b) recovering the trans-4-isopropylcyclohexane acid chloride.

2. The process of claim 1, wherein the organic amide is selected from the group consisting of N,N-dimethylacetamide, N-methylpyrrolidone and N,N-dimethylformamide.

3. The process of claim 1, wherein the combining is carried out with about 1 to about 5 acid equivalents of thionyl chloride, from about 0.05% to about 10% weight of the amide to the acid, and a temperature of from about 10° C. to about 60° C.

4. The process of claim 3, wherein the ratio of the cis isomer is less than about 0.03% weight to weight to the trans isomer.

5. The process of claim 1, wherein the combining results in a reaction mixture that is maintained for about 1 hour to about 5 hours.

6. The process of claim 1, wherein the combining is carried out in a solvent selected from the group consisting of aromatic and saturated hydrocarbons, esters and ethers.

7. A process for preparing nateglinide comprising the steps of:
   a) combining trans-4-isopropylcyclohexane carboxylic acid with thionyl chloride in the presence of a $C_1$ to a $C_6$ organic amide to obtain trans-4-isopropylcyclohexane acid chloride substantially free of its corresponding cis isomer; and
   b) converting the acid chloride to nateglinide; and
   c) recovering the nateglinide.

8. The process of claim 7, wherein the organic amide is selected from the group consisting of N,N-dimethylacetamide, N-methylpyrrolidone and N,N-dimethylformamide.

9. The process of claim 7, wherein the reacting is carried out with about 1 to about 5 acid equivalents of thionyl chloride, from about 0.05% to about 10% weight of the amide to the acid, and a temperature of from about 10° C. to about 60° C.

10. The process of claim 9, wherein the ratio of the cis isomer is less than about 0.03% (wt/wt) compared to its corresponding trans isomer.

11. The process of claim 7, further comprising the step of crystallizing/recrystallizing the nateglinide.

12. A process for preparing nateglinide in a two phase system comprising the steps of:
   a) preparing an aqueous solution of an alkaline earth or alkali metal salt of D-phenylalanine;
   b) combining the aqueous solution with a water immiscible organic solvent containing trans-4-isopropylcyclohexane acid chloride, to form an aqueous and an organic phase, wherein nateglinide forms through reaction between the D-phenylalanine and the trans-4-isopropylcyclohexane acid chloride; and
   c) recovering the nateglinide.

13. The process of claim 12, wherein a strong base is used to prepare the solution of the salt in water.

14. The process of claim 13, wherein the base is sodium or potassium hydroxide.

15. The process of claim 12, wherein the aqueous solution has a pH of at least about 8.

16. The process of claim 15, wherein the pH is at least about 12.

17. The process of claim 12, wherein the trans-4-isopropylcyclohexane acid chloride is substantially free of its corresponding cis isomer.

18. The process of claim 12, wherein the water immiscible organic solvent is a $C_5$ to a $C_{12}$ hydrocarbon.

19. The process of claim 18, wherein the hydrocarbon is aromatic.

20. The process of claim 19, wherein the hydrocarbon is toluene.

21. The process of claim 18, wherein the hydrocarbon is saturated.

22. The process of claim 21, wherein the hydrocarbon is heptane.

23. The process of claim 12, wherein the water immiscible organic solvent is an ester.

24. The process of claim 23, wherein the ester is ethyl acetate.

25. The process of claim 12, wherein the aqueous solution contains water free of a co-solvent.

26. The process of claim 12, wherein recovering involves precipitating nateglinide, and separating the precipitate.

27. The process of claim 26, wherein the nateglinide separated is nateglinide Form Z.

28. The process of claim 12, wherein recovering involves moving the nateglinide to the organic phase, and concentrating the organic phase.

29. The process of claim 28, wherein the moving is carried out through acidification of the aqueous phase.

30. The process of claim 29, wherein the acidification results in a pH of from about 1 to about 5.

31. The process of claim 30, wherein the pH is from about 2 to about 3.

32. The process of claim 12, wherein the trans-4-isopropylcyclohexane acid chloride is prepared by chlorinating trans-4-isopropylcyclohexane carboxylic acid with thionyl chloride in the presence of a $C_1$ to a $C_6$ organic amide.

33. The process of claim 12, further comprising the step of crystallizing/recrystallizing the nateglinide.

34. A process for preparing nateglinide comprising the steps of:
   a) preparing an aqueous solution of an alkaline earth or alkali metal salt of D-phenylalanine in water free of a co-solvent;
   b) adding trans-4-isopropylcyclohexane acid chloride as a neat reagent to the aqueous solution to form nateglinide; and
   c) recovering the nateglinide.

35. The process of claim 34, wherein a strong base is used to prepare the solution of the salt in water.

36. The process of claim 35, wherein the base is sodium or potassium hydroxide.

37. The process of claim 34, wherein the aqueous solution has a pH of at least about 8.

38. The process of claim 37, wherein the pH is at least about 12.

39. The process of claim 34, wherein the nateglinide recovered is substantially free of a dimer having the following structure:

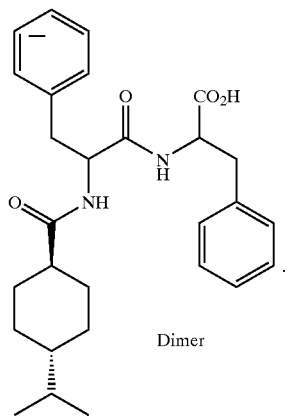

Dimer

40. The process of claim 39, wherein the dimer is present at a level of from about 0.04% to about 0.1% weight of the dimer to weight of nateglinide.

41. The process of claim 34, wherein the nateglinide has a purity of at least about 99%.

42. The process of claim 34, wherein the neat reagent added contains from about 0.05% to about 8% dimethyl formamide, weight to weight of dimethyl formamide to trans-4-isopropylcyclohexane acid chloride.

43. The process of claim 34, wherein the water contains less than about 1% v/v of any other solvent.

44. The process of claim 34, wherein the trans-4-isopropylcyclohexane acid chloride is prepared by chlorinating trans-4-isopropylcyclohexane carboxylic acid with thionyl chloride in the presence of a $C_1$ to a $C_6$ organic amide.

45. The process of claim 34, wherein recovering is carried out by acidification to obtain nateglinide as a precipitate, followed by separation of the nateglinide.

46. The process of claim 45, wherein the nateglinide recovered is nateglinide Form Z.

47. The process of claim 34, wherein recovering involves moving the nateglinide to an organic phase, and concentrating the organic phase.

48. The process of claim 34, further comprising the step of crystallizing/recrystallizing the nateglinide.

49. A process for preparing nateglinide comprising the steps of:
   a) combining a solution of a tri-alkyl amine salt of D-phenylalanine with trans-4-isopropylcyclohexane acid chloride in a $C_1$ to a $C_7$ amide to form nateglinide; and
   b) recovering the nateglinide.

50. The process of claim 49, wherein the tri-alkyl amine is tri-ethyl amine.

51. The process of claim 49, wherein the amide is selected from the group consisting of N,N-dimethyl formamide, N,N-dimethyl acetamide and N-methyl pyrolidone.

52. The process of claim 51, wherein the amide is N,N-dimethyl formamide.

53. A process for preparing nateglinide comprising the steps of:
   a) converting trans-4-isopropylcyclohexanecarboxylic acid to trans-4-isopropylcyclohexane acid chloride by reacting with thionyl chloride in the presence of an organic amide;
   b) adding the isopropylcyclohexane acid chloride to toluene, heptane, ethyl acetate or mixtures thereof;
   c) combining the toluene, heptane or ethyl acetate containing the isopropylcyclohexane acid chloride with an aqueous solution containing sodium salt of D-phenylalanine to form an aqueous and an organic phase, wherein nateglinide forms between the two phases; and
   d) recovering the nateglinide.

54. The process of claim 53, wherein recovering involves precipitation of nateglinide followed by separation of the precipitate.

55. The process of claim 53, further comprising the step of crystallizing/recrystallizing the nateglinide.

56. A process for preparing nateglinide comprising the steps of:
   a) converting trans-4-isopropylcyclohexanecarboxylic acid to trans-4-isopropylcyclohexane acid chloride by reaction with thionyl chloride in the presence of an organic amide;
   b) adding the trans-4-isopropylcyclohexane acid chloride to an aqueous solution of sodium or potassium salt of D-phenylalanine in water free of a co-solvent; and
   c) recovering the nateglinide.

57. A process for preparing nateglinide comprising the steps of:
   a) converting 4-isopropylcyclohexanecarboxylic acid to 4-isopropylcyclohexane acid chloride by reaction with thionyl chloride in the presence of an effective amount of an amide;

b) adding the isopropylcyclohexane acid chloride to a solution of sodium salt of D-phenylalanine in a mixture of acetone and water;

c) adding a water immiscible organic solvent to obtain an aqueous and an organic phase;

d) moving the nateglinide to the organic phase by reducing pH; and e) concentrating the organic phase.

* * * * *